United States Patent [19]

Chu

[11] 4,182,923
[45] * Jan. 8, 1980

[54] DISPROPORTIONATION OF TOLUENE

[75] Inventor: Chin-Chiun Chu, North Brunswick, N.J.

[73] Assignee: Mobil Oil Corporation, New York, N.Y.

[*] Notice: The portion of the term of this patent subsequent to Jul. 4, 1995, has been disclaimed.

[21] Appl. No.: 881,109

[22] Filed: Feb. 24, 1978

[51] Int. Cl.$^2$ .................................................. C07C 3/62
[52] U.S. Cl. ........................................................ 585/475
[58] Field of Search ..................................... 260/672 T

[56] References Cited
U.S. PATENT DOCUMENTS

| | | | |
|---|---|---|---|
| 4,011,276 | 3/1977 | Chu | 260/672 T |
| 4,016,219 | 4/1977 | Kaeding | 260/672 T |
| 4,098,837 | 7/1978 | Chu | 260/672 T |

*Primary Examiner*—C. Davis
*Attorney, Agent, or Firm*—Charles A. Huggett; Ronald J. Cier

[57] ABSTRACT

Disproportionation of toluene with high conversion thereof to produce benzene and xylenes rich in the para isomer is accomplished by subjecting toluene to disproportionation conditions in the presence of a catalyst comprising a crystalline aluminosilicate zeolite, said zeolite having a silica to alumina ratio of at least about 12 and a constraint index, as hereinafter defined, within the approximate range of 1 to 12, which catalyst has undergone prior modification by treatment with an ammonium hydrogen phosphate to deposit at least about 0.5 weight percent of phosphorus thereon.

13 Claims, No Drawings

DISPROPORTIONATION OF TOLUENE

BACKGROUND OF THE INVENTION

1. Field of the Invention

This invention relates to a process affording high activity for disproportionation of toluene utilizing a crystalline aluminosilicate zeolite catalyst modified with phosphorus as a result of treatment with an ammonium hydrogen phosphate to yield benzene and xylenes in which the proportion of para-xylene isomer is substantially in excess of its normal equilibrium concentration.

2. Description of the Prior Art

The disproportionation of aromatic hydrocarbons in the presence of zeolite catalysts has been described by Grandio et al. in the *Oil and Gas Journal*, Vol. 69, Number 48 (1971).

U.S. Pat. Nos. 3,126,422; 3,413,374; 3,598,878; 3,598,879 and 3,607,961 show vapor phase disproportionation of toluene over various catalysts.

U.S. Pat. No. 4,011,276 discloses disproportionation of toluene to produce benzene and xylenes rich in the para isomer with a catalyst comprising a crystalline aluminosilicate zeolite of the ZSM-5 type which has been modified by the addition thereto of a minor proportion of an oxide of phosphorus and a minor proportion of an oxide of magnesium. U.S. Pat. No. 4,016,219 discloses similar reaction but wherein the catalyst employed has been modified by the addition thereto of phosphorus in an amount of at least about 0.5 percent by weight. While the processes of each of these patents show selective production of para-xylene, such was obtained only by tolerating a very substantial reduction in toluene conversion, i.e., decrease in activity compared to disproportionation of toluene carried out under comparable conditions with the unmodified zeolite catalyst.

In these prior art processes, the xylene product produced either has the equilibrium composition of approximately 24 percent of para, 54 percent of meta and 22 percent of ortho or in those instances where the para isomer has been produced in an amount in excess of its equilibrium concentration, such was achieved only at great expense of activity, i.e., a very substantial reduction in toluene conversion. Of the xylene isomers, i.e., ortho-, meta- and para-xylene, meta-xylene is the least desired product, with ortho- and para-xylene being the more desired products. Para-xylene, in substantial yield, is of particular value being useful in the manufacture of terephthalic acid which is an intermediate in the manufacture of synthetic fibers such as "Dacron". Mixtures of xylene isomers either alone or in further admixture with ethylbenzene have previously been separated by expensive superfractionation and multistage refrigeration steps. Such process, as will be realized, has involved high operation costs and has a limited yield.

SUMMARY OF THE INVENTION

In accordance with the present invention, there has been discovered a process for disproportionating toluene with high conversion thereof to yield benzene and xylenes rich in the para isomer, preferably wherein the para-xylene content is in excess of 50 weight percent of the reaction product, by subjecting toluene to disproportionation conditions in the presence of a catalyst comprising a crystalline aluminosilicate zeolite, such zeolite having a silica to alumina ratio of at least about 12, a constraint index within the approximate range of 1 to 12, which catalyst has enhanced activity as a result of prior modification by treatment with an ammonium hydrogen phosphate to deposit at least about 0.5 weight percent of phosphorus thereon.

The present process comprises disproportionation of toluene in the presence of the specified catalyst at a temperature between about 390° F. (200° C.) and about 1400° F. (760° C.) at a pressure between atmospheric and about 1000 psig utilizing a feed weight hourly space velocity (WHSV) between about 0.08 and about 20. The latter WHSV is based upon the weight of catalyst composition, i.e., total weight of active catalyst and binder therefor. The effluent is separated and distilled to remove the desired products of benzene and xylenes and unreacted material, i.e., toluene, is recycled for further reaction.

DESCRIPTION OF SPECIFIC EMBODIMENTS

The crystalline aluminosilicate zeolite employed herein is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the crystalline free space.

The silica to alumina ratio referred to may be determined by conventional analysis. This ratio is meant to represent as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorp normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions although puckered structures exist such as TMA Offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \log_{10} \frac{\text{(fraction of n-hexane remaining)}}{\text{(fraction of 3-methylpentane remaining)}}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 100° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35 with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

Generally, however, the zeolite either directly or via initial ammonium exchange followed by calcination, is preferably hydrogen exchanged such that a predominate proportion of its exchangeable cations are hydrogen ions. In general, it is contemplated that more than 50 percent and preferably more than 75 percent of the cationic sites of the crystalline aluminosilicate zeolite will be occupied by hydrogen ions.

In practicing the desired conversion process, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families includes the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zironia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The above crystalline aluminosilicate zeolites employed are, in accordance with the present invention, contacted with a solution of an ammonium hydrogen phosphate. The latter may be either an ammonium dihydrogen phosphate $NH_4H_2PO_4$ or preferably a diammonium hydrogen phosphate $(NH_4)_2HPO_4$. A solution of such compound in a suitable solvent inert with respect to the ammonium hydrogen phosphate and the zeolite may be employed. Generally, the solvent is water.

Prior to reacting the zeolite with the ammonium hydrogen phosphate, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 1–5 hours but may be extended up to 24 hours or longer. While heating temperatures above about 500° C. can be employed, they are not necessary. At temperatures of about 1000° C., the crystal structure of the zeolite tends to deteriorate. After heating in air at elevated temperatures, phosphorus is present in oxide form.

The amount of phosphorus incorporated with the zeolite should be at least about 0.5 percent by weight. However, it is preferred that the amount of phosphorus in the zeolite be at least about 2 percent by weight, particularly when the same is combined with a binder, e.g., 35 weight percent of alumina. The amount of phosphorus can be as high as about 25 by weight or more depending on the amount and type of binder present.

Preferably, the amount of phosphorus added to the zeolite is between about 1 and about 15 percent by weight.

The amount of phosphorus incorporated with the zeolite by reaction with the ammonium hydrogen phosphate will depend upon several factors. One of these is the reaction time, i.e., the time that the zeolite and the ammonium phosphate are minimized in contact with each other. Generally, such contact time will be between about 0.25 and about 24 hours. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the ammonium hydrogen phosphate, the conditions of drying of the zeolite after reaction of the zeolite with the treating compound, and the amount and type of binder incorporated with the zeolite. Reaction temperature will generally be between about 20° and about 100° C. The concentration of the ammonium hydrogen phosphate in the reaction mixture is usually between about 5 and about 50 weight percent.

The process of this invention is conducted such that disproportionation of toluene is carried out in the vapor phase by contact in a reaction zone, such as, for example, a fixed bed of catalyst, under disproportionation effective conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline aluminosilicate zeolite, above-described, will be occupied by hydrogen ions.

The disproportionation process described herein may be carried out as a batch-type, semi-continuous or continuous operation utilizing a fixed or moving bed catalyst system. A preferred embodiment entails use of a fluidized catalyst zone wherein toluene is passed concurrently or countercurrently through a moving fluidized bed of the catalyst. The fluidized catalyst after use is conducted to a regeneration zone wherein coke is burned from the catalyst in an oxygen-containing atmosphere, e.g., air, at an elevated temperature, after which the regenerated catalyst is recycled to the conversion zone for further contact with the toluene feed.

The following examples will serve to illustrate the process of the invention without limiting the same:

EXAMPLE 1

This example serves to illustrate disproportionation of toluene in the presence of a catalyst of HZSM-5 which has not been modified with phosphorus.

A catalyst containing 65 weight percent acid ZSM-5 and 35 weight percent alumina was prepared as follows:

A sodium silicate solution was prepared by mixing 8440 lb. of sodium silicate (Q Brand—28.9 weight percent $SiO_2$, 8.9 weight percent $Na_2O$ and 62.2 weight percent $H_2O$) and 586 gallons of water. After addition of 24 lb. of a dispersant of a sodium salt of polymerized substituted benzenoid alkyl sulfonic acid combined with an inert inorganic suspending agent (Daxad 27), the solution was cooled to approximately 55° F. An acid alum solution was prepared by dissolving 305 lb. aluminum sulfate (17.2 $Al_2O_3$), 733 lb. sulfuric acid (93%) and 377 lb. sodium chloride in 602 gallons of water. The solutions were gelled in a mixing nozzle and discharged into a stirred autoclave. During this mixing operation, 1200 lb. of sodium chloride was added to the gel and thoroughly mixed in the vessel. The resulting gel was thoroughly agitated and heated to 200° F. in the closed vessel. After reducing agitation, an organic solution prepared by mixing 568 lb. tri-n-propylamine, 488 lb. n-propyl bromide and 940 lb. methyl ethyl ketone was added to the gel. This mixture was reacted for 14 hours at a temperature of 200°–210° F. At the end of this period, agitation was increased and these conditions maintained until the crystallinity of the product reached at least 65% ZSM-5 as determined by X-ray diffraction. Temperature was then increased to 320° F. until crystallization was complete. The residual organics were flashed from the autoclave and the product slurry was cooled.

The product was washed by decantation using a flocculant of polyammonium bisulfate. The washed product containing less than 1% sodium was filtered and dried. The weight of dried zeolite was approximately 2300 lb.

The dried product was mixed with alpha alumina monohydrate and water (65% zeolite, 35% alumina binder on ignited basis) then extruded to form a 1/16 inch pellet with particle density <0.98 gram/cc and crush strength of >20 lb./linear inch.

After drying, the extruded pellets were calcined in nitrogen (700–1000 SCFM) for 3 hours at 1000° F., cooled and ambient air was passed through the bed for 5 hours. The pellets were then ammonium exchanged for one hour at ambient temperature (240 lb. ammonium nitrate dissolved in approximately 800 gallons of deionized water). The exchange was repeated and the pellets washed and dried. Sodium level in the exchanged pellets was less than 0.05 weight percent.

The dried pellets were calcined in a nitrogen-air mixture (10–12.5% air–90–87.5% nitrogen) for 6 hours at 1000° F. and cooled in notrogen alone.

This catalyst was used for disproportionating toluene by passing the same over 6.0 grams of the catalyst at a weight hourly space velocity of 3.5–3.6 at a temperature between 450° C. and 600° C. The conditions and results are summarized in Table I below.

TABLE I

| Temp, °C. | WHSV | Tol. Conv. Mole % | Selectivity, % | | % Para in Xylene Product |
|---|---|---|---|---|---|
| | | | Benzene | Xylenes | |
| 450 | 3.6 | 7.4 | 43.5 | 55.5 | 24.7 |
| 500 | 3.5 | 20.5 | 44.6 | 53.8 | 24.5 |
| 550 | 3.5 | 38.8 | 48.0 | 48.8 | 24.2 |
| 600 | 3.5 | 49.2 | 54.4 | 41.7 | 24.1 |

It will be seen from the above-tabulated data obtained from use of the unmodified HZSM-5 catalyst that the amount of para-xylene in the xylene product produced essentially corresponds to that of equilibrium mixtures, i.e., there has been no selective production of para-xylene.

EXAMPLE 2

HZSM-5 in the form of an extrudate, containing 35 percent aluminum binder, in an amount of 12 grams was added to a solution of 5 grams of diammonium hydrogen phosphate [$(NH_4)_2HPO_4$] in 20 mls. of water. After filtration, drying and calcination at 500° C. for 2 hours, a zeolite catalyst containing 3.6 weight percent of phosphorus was obtained.

EXAMPLES 3-6

Disproportionation of toluene was effected by passing toluene over 5 grams of the catalyst prepared as in Example 2 and the results compared with a sample of the unmodified HZSM-5 extrudate from which the catalyst of Example 2 was modified, at a WHSV of 3.5 and the temperatures shown in Table II below:

TABLE II

| | | Catalyst of Example 2 | | Unmodified HZSM-5 | |
|---|---|---|---|---|---|
| Example | Temp. °C. | % Toluene Conv. | % p-Xylene in Xylenes | % Toluene Conv. | % p-Xylene in Xylenes |
| 3 | 475 | 19.3 | 34.0 | 17.7 | 25.3 |
| 4 | 500 | 27.2 | 32.5 | 19.6 | 25.4 |
| 5 | 525 | 36.4 | 30.2 | 28.6 | 25.0 |
| 6 | 550 | 43.0 | 28.4 | 37.8 | 24.7 |

It will be evident from the above data that the ZSM-5 catalyst which had undergone modification with an ammonium hydrogen phosphate to deposit a small amount of phosphorus thereon gave higher activity for toluene disproportionation as well as higher selectivity to para-xylene under identical conversion conditions than the unmodified ZSM-5 catalyst.

EXAMPLE 7

HZSM-5, in the form of an extrudate, containing 35 weight percent alumina binder, in an amount of 30 grams was treated with a solution of 20 grams of diammonium hydrogen phosphate in 50 mls. of water. After filtration, drying and calcination as in Example 2, a resulting catalyst product was obtained containing 5.5 weight percent phosphorus.

EXAMPLES 8-11

Disproportionation of toluene was conducted by passing toluene over 5 grams of the catalyst prepared as in Example 7, as well as the unmodified HZSM-5 extrudate from which catalyst of Example 7 was modified, at a WHSV of 3.5 and the temperatures shown in Table III below:

TABLE III

| | | Catalyst of Example 7 | | Unmodified HZSM-5 | |
|---|---|---|---|---|---|
| Example | Temp. °C. | % Toluene Conv. | % of p-Xylene in Xylenes | % Toluene Conv. | % of P-Xylene in Xylenes |
| 8 | 475 | 14.7 | 30.0 | 11.3 | 24.5 |
| 9 | 500 | 22.2 | 29.4 | 19.7 | 24.4 |
| 10 | 525 | 30.1 | 28.6 | 27.7 | 24.1 |
| 11 | 550 | 39.1 | 27.3 | 31.1 | 24.1 |

Again, it will be seen that the ZSM-5 catalyst modified by treatment with ammonium hydrogen phosphate afforded higher toluene conversion along with higher selectivity to para-xylene, under identical conditions of reaction, compared to the unmodified ZSM-5 catalyst.

EXAMPLE 12

Another sample of HZSM-5, in the form of an extrudate, in an amount of 24.0 grams was treated with solution of 32.0 grams of diammonium hydrogen phosphate in 40.0 mls. of water. After filtration, drying and calcination as in Example 2, the resulting catalyst product was found to contain 8.9 weight percent phosphorus.

EXAMPLES 13-16

Disproportionation of toluene was carried out by passing toluene over 5 grams of the catalyst prepared as in Example 12, as well as the unmodified HZSM-5 extrudate from which catalyst of Example 12 was modified, at a WHSV Of 3.5 and the temperatures shown in Table IV below:

TABLE IV

| | | Catalyst of Example 12 | | Unmodified HZSM-5 | |
|---|---|---|---|---|---|
| Example | Temp. °C. | % Tolune Conv. | % of p-Xylene in Xylenes | % Toluene Conv. | % of p-Xylene in Xylenes |
| 13 | 475 | 18.4 | 27.7 | 9.7 | 24.5 |
| 14 | 500 | 23.8 | 27.8 | 16.0 | 24.6 |
| 15 | 525 | 31.4 | 27.3 | 23.2 | 24.5 |
| 16 | 550 | 37.8 | 26.6 | 33.7 | 24.2 |

Once again, it will be seen that the ammonium hydrogen phosphate modified catalyst provided a higher conversion of toluene and higher selectivity of para-xylene compared with the unmodified ZSM-5 catalyst.

EXAMPLE 17

An extrudate of HZSM-5, containing 35 weight percent of alumina binder, in an amount of 6 grams was added to a solution of 1.5 grams of 85% phosphoric acid ($H_3PO_4$) in 10 ml. of water at room temperature and allowed to stand for 16 hours. After decantation and drying at 120° C., the residue was calcined at 500° C. overnight. The resulting zeolite contained 4.92 weight percent phosphorus.

EXAMPLES 18-19

Toluene was disproportionated by conducting a stream thereof over a 5 gram sample of the catalyst of Example 17 and the results compared with the unmodified HZSM-5 extrudate from which catalysts of Example 17 was prepared at a WHSV of 3.5 and the temperatures shown in Table V below:

TABLE V

| Example | Temp. °C. | Catalyst of Example 17 | | Unmodified HZSM-5 | |
|---|---|---|---|---|---|
| | | % Toluene Conv. | % of p-Xylene in Xylenes | % Toluene | % of p-Xylene in Xylenes |
| 18 | 500 | 20.9 | 24.3 | 29.1 | 24.3 |
| 19 | 550 | 39.2 | 24.1 | 45.5 | 24.1 |

It will be seen from the above data that the phosphorus-modified HZSM-5 catalyst utilizing phosphoric acid, as distinguished from an ammonium hydrogen phosphate, afforded no increase in para-xylene selectivity with a substantial decrease in toluene conversion over the unmodified HZSM-5 catalyst.

EXAMPLE 20

A phosphorus-containing HZSM-5 catalyst was prepared as in Example 17 except that 4 grams of 85% phosphoric acid was used. The resulting zeolite product was found to contain 8.59 weight percent phosphorus.

EXAMPLES 21-22

Toluene was disproportionated over the catalyst of Example 20 at the conditions specified in Examples 18-19 with the results set forth in Table VI below:

TABLE VI

| Example | Temp. °C. | Catalyst of Example 20 | | Unmodified HZSM-5 | |
|---|---|---|---|---|---|
| | | % Toluene Conv. | % of p-Xylene in Xylenes | % Toluene Conv. | % of p-Xylene in Xylenes |
| 21 | 500 | 9 | 24.7 | 29.1 | 24.3 |
| 22 | 550 | 23.1 | 24.4 | 45.5 | 24.1 |

It will again be evident from the above data that the amount of para-xylene produced utilizing the HZSM-5 catalyst modified by treatment with phosphoric acid was no greater than the normal concentration of para-xylene contained in the equilibrium isomer mixture and further that such modified catalyst resulted in lower conversion of toluene compared to the unmodified catalyst.

It is to be understood that the foregoing description is merely illustrative of preferred embodiments of the invention of which many variations may be made by those skilled in the art within the scope of the following claims without departing from the spirit thereof.

What is claimed is:

1. A process for effecting disproportionation of toluene with high conversion thereof to produce benzene and xylenes in which the proportion of para-xylene is in excess of its normal equilibrium concentration which comprises contacting toluene under conditions effective for accomplishing said disproportionation in the presence of a catalyst comprising a crystalline aluminosilicate zeolite, said zeolite having a silica to alumina ratio of at least about 12, a constraint index within the approximate range of 1 to 12, said catalyst having enhanced activity as a result of prior modification by treatment with an ammonium hydrogen phosphate to deposit at least about 0.5 weight percent of phosphorus thereon.

2. The process of claim 1 wherein said ammonium hydrogen phosphate is diammonium hydrogen phosphate.

3. The process of claim 1 wherein said ammonium hydrogen phosphate is ammonium dihydrogen phosphate.

4. The process of claim 1 wherein said crystalline aluminosilicate is ZSM-5.

5. The process of claim 1 wherein said phosphorus is present in an amount between about 0.5 and about 25 weight percent.

6. The process of claim 1 wherein said crystalline aluminosilicate zeolite is characterized by a silica/alumina ratio in excess of 30.

7. The process of claim 1 wherein the disproportionation conditions include a temperature of between about 390° F. and about 1400° F., a pressure between atmospheric and about 1000 psig and a weight hourly space velocity between about 0.08 and about 20.

8. The process of claim 1 wherein the crystalline aluminosilicate zeolite is combined in an amount between about 1 and about 90 weight percent in a binder therefor.

9. The process of claim 8 wherein said binder is alumina.

10. The process of claim 1 wherein the crystalline aluminosilicate zeolite is predominately in the hydrogen form.

11. The process of claim 4 wherein the ZSM-5 zeolite is predominately in the hydrogen form.

12. The process of claim 7 wherein the crystalline aluminosilicate zeolite is ZSM-5.

13. The process of claim 12 wherein the ZSM-5 zeolite is predominately in the hydrogen form.

* * * * *